(12) United States Patent
Khair et al.

(10) Patent No.: US 12,274,555 B2
(45) Date of Patent: Apr. 15, 2025

(54) MULTI-SENSOR PATCH

(71) Applicant: GE Precision Healthcare LLC, Waukesha, WI (US)

(72) Inventors: Mohammad Khair, Whitefish Bay, WI (US); Steven M. Falk, Baltimore, MD (US); Jean-Francois Pieri, Nottingham (GB)

(73) Assignee: GE Precision Healthcare LLC, Waukesha, WI (US)

( * ) Notice: Subject to any disclaimer, the term of this patent is extended or adjusted under 35 U.S.C. 154(b) by 25 days.

(21) Appl. No.: 18/344,744

(22) Filed: Jun. 29, 2023

(65) Prior Publication Data

US 2023/0337957 A1 Oct. 26, 2023

Related U.S. Application Data

(63) Continuation of application No. 16/868,865, filed on May 7, 2020, now Pat. No. 11,744,501.

(51) Int. Cl.
| | |
|---|---|
| A61B 5/288 | (2021.01) |
| A61B 5/00 | (2006.01) |
| A61B 5/024 | (2006.01) |
| A61B 5/1455 | (2006.01) |
| A61B 5/1464 | (2006.01) |
| A61B 5/352 | (2021.01) |

(52) U.S. Cl.
CPC .......... *A61B 5/288* (2021.01); *A61B 5/02411* (2013.01); *A61B 5/02416* (2013.01); *A61B 5/1455* (2013.01); *A61B 5/1464* (2013.01); *A61B 5/352* (2021.01); *A61B 5/6833* (2013.01); *A61B 5/7207* (2013.01); *A61B 2503/02* (2013.01); *A61B 2562/0219* (2013.01); *A61B 2562/0233* (2013.01); *A61B 2562/164* (2013.01)

(58) Field of Classification Search
None
See application file for complete search history.

(56) References Cited

U.S. PATENT DOCUMENTS

| | | | |
|---|---|---|---|
| 2010/0185108 A1* | 7/2010 | Vullings | A61B 5/4362 600/511 |
| 2011/0218413 A1* | 9/2011 | Wang | A61B 5/02411 600/338 |
| 2016/0262649 A1* | 9/2016 | Hayes-Gill | A61B 5/339 |
| 2017/0281087 A1* | 10/2017 | Workman | A61B 8/02 |
| 2019/0343437 A1* | 11/2019 | Ray | A61B 5/02055 |
| 2020/0289047 A1* | 9/2020 | Qi | A61B 5/7278 |

* cited by examiner

*Primary Examiner* — Michael W Kahelin

(57) ABSTRACT

A method of sensing the heart rate and blood oxygen saturation of a maternal patient and a fetal patient can include obtaining maternal electrocardiogram (mECG) data and fetal electrocardiogram (fECG) data with a plurality of electrodes. The method can also include obtaining photosignal data with an optical sensor, the photosignal data including a maternal photosignal component and a fetal photosignal component. Additionally, the method can include applying mECG to the photosignal data to calculate maternal photoplesthograph (mPPG) data, applying the mPPG to the photosignal data to remove the maternal photosignal component from the photosignal data, and applying the fECG to remaining photosignal data to calculate fetal photoplesthograph (fPPG) data.

14 Claims, 6 Drawing Sheets

MULTI-SENSOR PATCH

CROSS-REFERENCE TO RELATED APPLICATIONS

The present application is a continuation of and claims priority to U.S. patent application Ser. No. 16/868,865, now U.S. Pat. No. 11,744,501, titled "Multi-Sensor Patch", filed May 7, 2020, the contents of which are incorporated by reference herein.

BACKGROUND

The present disclosure relates to maternal and fetal monitoring. More specifically, the present disclosure relates to an apparatus and method for monitoring a plurality of physiological parameters of maternal and fetal patients.

Medical devices are known that can be used to detect a fetal electrocardiogram (fECG) without making physical contact with the fetus. Such devices use electrodes that are placed on the mother's skin to detect electrophysiological signals. The maternal electrocardiogram (mECG) will also tend to be detected by the electrodes, and it can be challenging to separate the fECG from the mECG. The electrical signals detected by the electrodes can be processed to determine: the fetal heart rate (from the fECG), the maternal heart rate (from the mECG). Maternal contractions, often referred to as uterine activity (UA) can be determined by electrohysterography (changes in electrical potential due to uterine contractions), which can be detected by the electrodes.

WO2009/150440 discloses a multi-electrode patch for use in fetal heart rate monitoring, the patch comprising a flexible substrate attachable to the skin of a pregnant subject. Three sensing electrodes are positioned on the flexible substructure to approximate an arc that is substantially the same length as the arc formed by a uterus fundus of a pregnant subject. Connection ports are provided by which each sensing electrode may be connected to a fetal heart rate monitor which receives the electrical signals from the electrodes and determines the fetal heart rate from the fECG, maternal heart rate from the mECG, and UA from the electrohysterogram. A multi-electrode patch is disclosed that includes integrated circuitry configured to amplify and filter a detected fECG signal.

EP 1 854 403 discloses a radial electrode assembly for monitoring fECG and mECG signals. The assembly comprises a flexible substrate defining a central focal point, and a plurality of electrodes disposed on the periphery of the flexible substrate, at a substantially equal fixed radial distance from the focal point.

US20160262649 discloses a multi-electrode patch for abdominal electrophysiological detection. The patch has a flexible substrate interconnecting multiple electrodes and a module unit for removably engaging with an electronic readout device for detecting a maternal and/or fetal electrophysiological signal from the electrodes. The module has a mechanical module unit for removable mechanical engagement with a housing of the readout device, and an electrical module unit for making an electrical connection from the electrodes to the readout device. The patch may be flexible in a manner that allows variation in the relative positioning between the electrodes.

Although the solutions noted above can be used for maternal and fetal monitoring, such systems are limited to monitoring ECG and ElectroHysterogram, and more robust patient monitoring is desired.

BRIEF DISCLOSURE

An exemplary embodiment of a multi-sensor patch for simultaneous abdominal monitoring of maternal and fetal physiological data includes a multi-layer flexible substrate. The multi-layer flexible substrate includes a center region and a plurality of electrode regions. A conductive layer of the flexile substrate providing an electrical connection between each of the plurality of electrode regions and the center region. A plurality of electrodes are formed into the flexible substrate. An electrode of the plurality of electrodes is located in each of the electrode regions. At least one auxiliary sensor is connected to the multi-layer flexible substrate. The at least one auxiliary sensor may be an optical sensor. A module unit is connected to the conductive layer at the center region. The module unit is configured to receive biopotential physiological data from the plurality of electrodes and photosignal data from the optical sensor of the at least one auxiliary sensor. The module unit calculates at least fetal heart rate (fHR), maternal heart rate (mHR), and uterine activity (UA) from the biopotential physiological data and fHR, mHR, and $SpO_2$ from the photosignal data.

In further exemplary embodiments of the multi-sensor patch, the plurality of electrodes, the conductive layer, and at least portions of the auxiliary sensor may be printed from conductive ink. The at least one auxiliary sensor may further include a microphone, a piezoelectric sensor, a strain gauge, an accelerometer, and/or a gyroscope. The physiological data from the auxiliary sensor may be used by the module unit to calculate the fHR, mHR, and UA. The module unit may use the physiological data from the auxiliary sensor of a strain gauge to further calculate UA. In combination with the strain gauge the at least one auxiliary sensor may include a microphone. The module unit may further use the physiological data from the microphone to further calculate fHR and mHR.

In still further exemplary embodiments at the least one auxiliary sensor is located in the module unit. The at least one auxiliary sensor located in the module unit may include an ultrasound, a pulse oximeter, or a temperature sensor. The module unit may further calculate a heart rate from the biopotential physiological data and the auxiliary sensor physiological data either in combination or as independent sources of data. The module unit may further be configured to receive an input selection from a user. Upon receipt of such input selection, the module unit may switch from a calculation of UA that includes the biopotential physiological data to a calculation of UA based upon the auxiliary physiological data while producing a calculated UA output in a real time or near real-time refresh rate.

In further examples of the multi-sensor patch, the controller operates to select segments of the at least one of the biopotential physiological signals and auxiliary physiological signals. The controller operates to create a patient specific model from the selected segments. The controller may operate to identify R-waves in the biopotential physiological signals and to select segments of the auxiliary physiological signals corresponding to fetal pulses in the auxiliary physiological signals. The patient specific model may be a pulse model of a fetal patient. The controller may operate to identify R-waves in the biopotential physiological signals and to select segments of the motion physiological signals corresponding to maternal pulses in the auxiliary physiological signals. The patient specific model may be a pulse model of a maternal patient. The controller may operate to apply the patient specific model to the auxiliary physiological signals to remove maternal contribution to the motion physiological signals, isolating the fetal contribution to the motion physiological signals.

DETAILED DISCLOSURE

Figure 1:
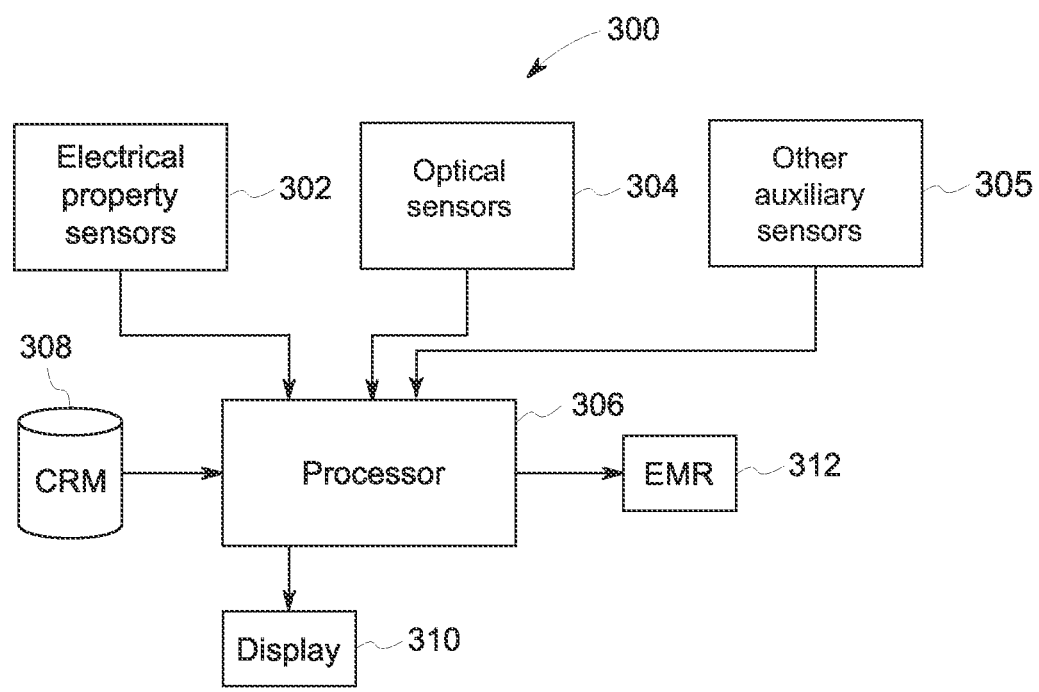
FIG. 1 is a system diagram of an exemplary embodiment of a system for monitoring a maternal patient and a fetal patient.

Common solutions for monitoring of maternal and fetal patients, include the use of ultrasound to detect fetal heartrate (fHR) and maternal heartrate (mHR) and a tocodynamometer to detect uterine activity. As noted above, electrode base solutions are available, although there are limitations, to bio potential based systems. Currently biopotential maternal and fetal monitors exemplarily use five silver/silver chloride wet electrodes to collect biopotentials from which measurements of fHR, mHR, as well as uterine activity are derived by computer processing of the collected bio potentials which include electrocardiographic data of both the maternal and fetal patients as well as uterine electromyographic data from which contractions are identified.

However, while the available electrode based solutions have advantages of disposability and ease of use, the present inventors have identified problems with the available systems that can be improved upon. It has been observed by the Inventors that the fHR as measured by the collected bio potentials can be lost when the fetus us surrounded by too much vernix caseosa. The vernix caseosa, or vernix, is the fatty deposit around the fetal patient which helps to protect the fetus during birth. Dependent upon the thickness and distribution of the vernix and position of the patient, this can lead to signal loss of the fetal ECG from which the fetal heartrate is derived. The fetal ECG can also be lost if there is a significant amount of skeletal electromyogram (EMG) noise. These signal loses may be relatively short in duration, but can be unpredictable in occurrence and may occur at inopportune times or may lead to unnecessary concern or worry among the maternal patient and/or caregivers.

Additionally, while biopotential measurement has been shown to be effective in the detection of contraction occurrences, the biopotential measurements have limited ability to detect contraction strength. At best, biopotentials may serve as a basis for comparative presentations of contraction strength without an ability for calibration or base line contraction strength determinations.

Finally, while currently available biopotential measurements of maternal and fetal heartrate as well as uterine activity are found to be accurate, due to the volume of bio potentials simultaneously acquired by such electrodes, intensive signal processing is required to isolate fHR, mHR, and UA from the collected signals. Due to this signal processing, the reported fHR, mHR, and UA are often presented on a delay. While in many patient monitoring settings this delay is acceptable as the fHR, mHR, and UA parameters are used as a general evaluation of fetal and maternal patient health, as well as the progression of labor, in some instances, patient information in real time or near real time is desired. An example of one such time in the care for the fetal and maternal patients, is during the placement of the epidural catheter. Due to the nature of epidural catheter placement into communication with the epidural space of the spine, real time or near real time identification of uterine activity is desired such as to avoid or limit maternal patient movement during the placement of the epidural catheter.

Therefore, the inventors have discovered that it is desirable to address the forgoing problems with current biopotential monitoring fetal and maternal patient monitoring systems, while maintaining a convenient, comfortable, and disposable patch form.

The biopotential base maternal and fetal monitor can thus be improved by the incorporation of one or more non-biopotential based systems to provide further measurement of maternal and/or fetal motion, maternal and/or fetal heart rate, and/or uterine activity.

As will be described in further detail herein, the combination of biopotential data and other auxiliary physiological data provides for improved monitoring of fetal and maternal health in addition to addressing all of the problems as identified above. Maternal and/or fetal patient specific models can be created as described in further detail herein through the use of determinations from one signal as the true or confirming signal to extract segments of another corresponding signal for model development. Models created over time through learning between the signals from two types of sensors can be used to enhance the individual performance of fHR, mHR, or UA determinations made from two different signal types. One example includes the use of an exact time location of an mECG wave to detect directly from the photosignals or to build a photosignal model of the maternal pulse as obtained from an auxiliary sensor signal in the form of photosignals obtained using photoemitters and photodetectors, as in the case of an $SpO_2$ sensor. Maternal pulse measurements provide an alternative and confirming measurement of mHR. Maternal pulse models can be used to then improve the isolation of fetal pulse signals from the mixed photosignal. Use of an exact time location of an fECG wave can similarly be used to detect directly or to build a photosignal model to improve fetal pulse detection. Fetal pulse measurements provide an alternative and confirming measurement of fHR. Improved detection of maternal and fetal pulses in photosignals further improves calculation of maternal and fetal $SpO_2$ values. In another example, an auxiliary sensor providing an accelerometer signal can be used to identify periods of maternal motion artifact from which portions of the photosignal can be rejected, improving accuracy of $SpO_2$ calculations. Similarly, periods of fetal motion artifact can be determined from the fECG and portions of the photosignal can thus be rejected, improving accuracy of $fSpO_2$ calculations.

FIG. 1 depicts a system diagram of a monitoring system 300 for maternal and fetal patients. The system 300 is provided in schematic form and it will be recognized by a person of ordinary skill in the art that in such system 300 may be implemented in a variety of manners, including the distribution and interconnection of components provided in FIG. 1 as so much as various components may be provided in one or more physical devices while being communicatively connected generally in the manner as shown in FIG. 1. As noted above, the system 300 includes electrical property sensors 302, for example the biopotential electrodes as disclosed above as well as will be described in further detail herein. These electrical property sensors 302 collect biopotentials from the skin of the maternal patient, which include biopotential signals from both the maternal and fetal patients.

The system 300 also includes an auxiliary sensor of optical sensor 304, which will be explained in more detail herein, and optionally, other auxiliary sensors 305. Other auxiliary sensors 305 may include ultrasound sensors, microphones, accelerometers, piezoelectric sensors, strain gauges, and other sensors that will be recognized by a person of ordinary skill in the art. The optical sensors 304 and other auxiliary sensors 305 are used to obtain signals indicative of mechanical motion by the maternal and/or fetal patients, for example but not limited to, heart contractions, blood flow, or uterine contractions. Optical signals can also be affected by tissue absorbance of photon energy due to metabolite content, for example Lactate, or blood gas content, for example Oxygen.

The signals obtained by the electrical property sensors 302 and the optical sensors 304 and any other auxiliary sensors 305 are provided to a controller 306. The controller 306 may be any of a variety of controllers, microcontrollers, processors, or integrated circuits as known in the art of physiological sensing for collection and/or analysis of physiological data. The controller 306 is able to collect data from the sensors either in analog or digital format. In embodiments where the data is collected in analog format, an internal or external analog converter can be used. The controller 306 is communicatively connected to a computer readable medium (CRM) 308 which is a non-transitory computer readable medium upon which computer readable code embodying software programs containing algorithm and/or software modules containing algorithms which upon execution by the controller 306 cause the controller to carry out the calculations and functions as described in further detail herein. The CRM 308 may be internal or external to the controller 306. In exemplary embodiments, the software and software modules as executed by the controller 306 are such as to isolate and analyze particular signals within the signals obtained from the electrical property sensors 302 as well as those obtained from the optical sensors 304 and any other auxiliary sensors in order to produce calculations of various output physiological parameters of the patient as described herein based upon the isolated and analyzed signals from the electrical property sensors 302, optical sensors 304, and any other auxiliary sensors 305. The controller 306 provides the calculated physiological parameter values to a display 310 which may operate to present one or more of the calculated values in a visually perceptible manner or stored at a patient electronic medical record (EMR) 312, stored at a non-transient computer data storage medium. The controller 306 may provide the calculated physiological parameter values across a wired or wireless connection and therefore, the display 310 or the EMR 312 may be physically connected to the controller 306, or may be located remote from the controller 306.

As noted above, it will be recognized that in embodiments, the electrical property sensors 302 and the optical sensors 304 and any other auxiliary sensors 305 may be integrated into the same patch of sensors as will be described in further detail herein, or may be provided as separate components. Additionally, the controller 306 and/or computer readable medium 308 may be integrated with such a patch containing the electrical property sensors 302 and the optical sensors 304 while in other embodiments, the system 300 may include additional instrumentation such as to transmit the signals acquired from the electrical property sensors 302 and the optical sensors 304 and any other auxiliary sensors 305 to be controller 306 which may be located remotely from the sensor. Still further configurations of the components as depicted in the system 300 as well as those system which include more of fewer components than those depicted in FIG. 1, will be recognized from the present disclosure while remaining within the scope of the present disclosure.

Figure 2:
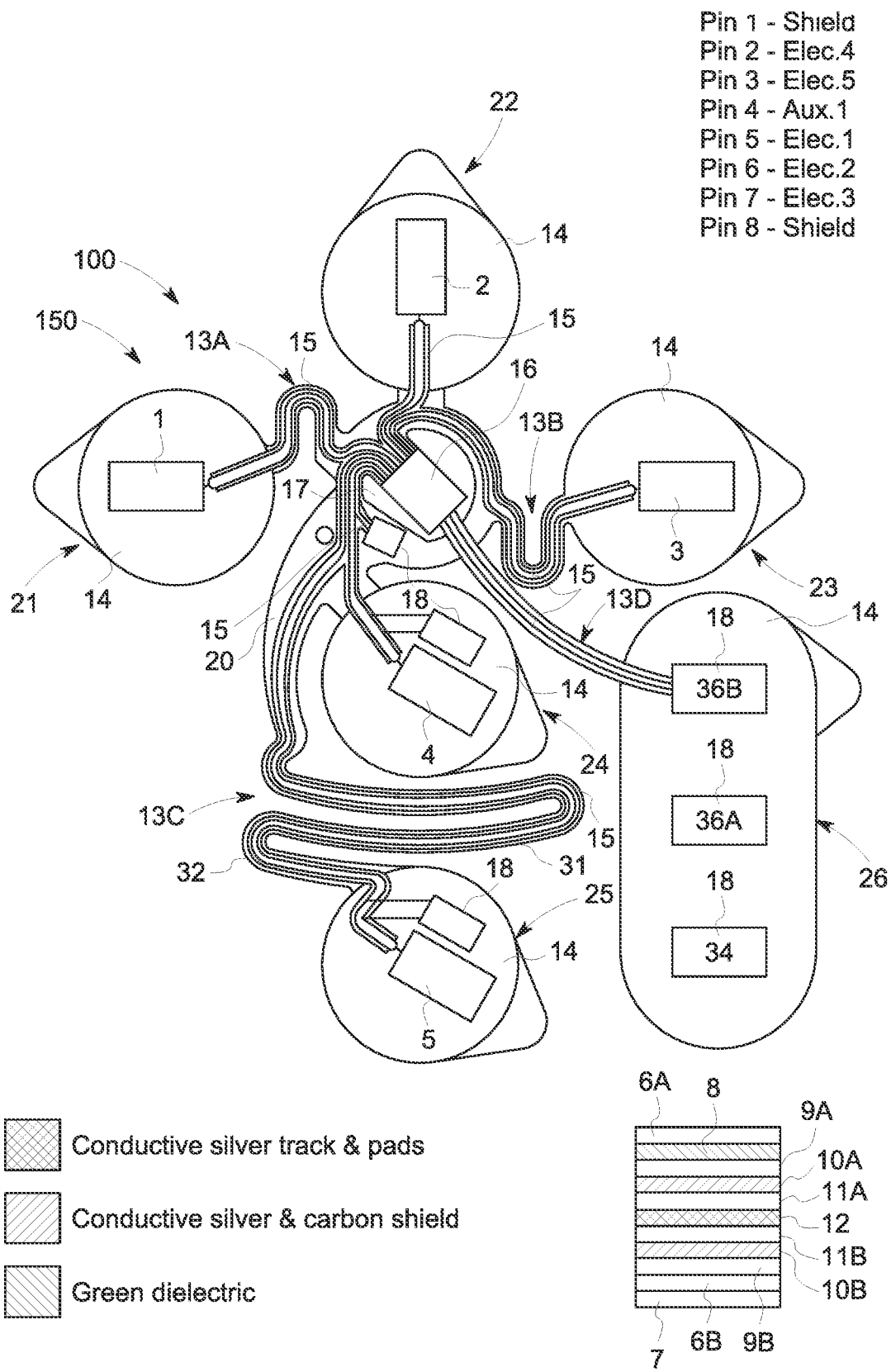
FIG. 2 is a layout diagram of an exemplary embodiment of a patch.

Referring to FIG. 2, a patch 150 exemplary of embodiments is shown. The patch 150 includes a flexible substrate 100, viewed from the side that is to be facing the abdomen, in use. The flexible substrate 100 comprises a plurality of layers 6-12. The layers 6-12 are patterned so as to define the shape of the substrate 100, and to form electrodes 1-5. Each electrode 1-5 is connected via a conducting track 15 to a connection hub 16, for electrically connecting electrodes 1-5 to a readout device (not shown). In embodiments as represented in FIG. 1, the substrate 100 may further be shaped to provide for a plurality of sensors, including, and in addition to electrodes 1-5. The plurality of sensors, as described in further detail herein may include at least one auxiliary sensor 18, although in embodiments more auxiliary sensors 18 may be found in the plurality of sensors. In embodiments, the conducting track 15 may be provided to electrically connect the one or more auxiliary sensors 18 to the connection hub 16. As previously noted, the one or more auxiliary sensors 18 may include one or more types of sensors configured to produce a signal indicative of the mechanical motion of the fetal patient and/or the maternal patient. Non-limiting embodiments of mechanical motion of the fetal patient may include fetal motion and/or kick counting, or fetal heart rate as monitored by fetal heart sounds, fetal heart movement, or fetal blood movement. Non-limiting embodiments of mechanical motion of the maternal patient may include maternal respiration movement or sounds, maternal heart sounds, maternal blood movement or sound, and maternal uterine contractions.

The electrodes 1-5 and/or the conducting tracks 15 and/or the auxiliary sensor 18 are formed from the signal layer 12, which includes silver ink or another material with the electrical and/or mechanical properties to form a sensor in the signal layer. For example, the conducting film used can be silver chloride which provides a good stoichiometric match to saline based electrode gels. A silver-containing ink may be used in particular to print the conducting tracks 15 and/or signal layer 12. As noted above, in exemplary and non-limiting embodiments, the auxiliary sensor 18, may be any of a strain gauge, a piezoelectric sensor, an accelerometer, a microphone, temperature sensor, SpO2 sensor, an ultrasound Doppler, a capacitive micromachined ultrasonic transducer, or other sensors as will be recognized by a person of ordinary skill in the art in view of the present disclosure. As will be discussed in further detail herein, the auxiliary sensor 18 may be formed from the signal layer 12 and/or printed from the silver containing ink. In other embodiments, the auxiliary sensor 18 may be a separately formed component and the signal layer 12 provides the conducting track 15 and/or a mounting or connection pad or contact.

As previously described auxiliary sensor 18, including at least an optical sensor, may be located in a variety of locations within the patch 150. FIG. 2 provides three exemplary locations for the optical sensor 18 or other auxiliary sensors, these include placing the optical sensor 18 in one or more of the patch regions 21-25 which contain the electrodes 1-5, in a central patch region 20 of the substrate, or in a dedicated sensor patch region 26 of the substrate 100. However, it will be recognized that embodiments may include auxiliary sensors 18 including the optical sensor at one of these locations, at all of these locations, or at other locations. Such other locations may include, but are not limited to within the connection hub 16 or within the readout device 200 as will be described in further detail herein, for example with respect to FIGS. 3 and 4.

An insulating dielectric layer 11A, 11B is arranged on each respective side of the signal layer 12. The insulating dielectric layers 11A, 11B have a similar pattern to the conducting tracks 15 of the signal layer 12. The insulating layers 11A, 11B substantially overlay the conducting tracks 15, and are oversized relative thereto. The insulating layers 11A, 11B completely cover the conducting tracks between the plurality of sensors and the connection hub 16, while leaving the signal layer 12 exposed at the electrodes, auxiliary sensor(s) and connection hub 16.

A graphite layer 10A, 10B is in contact with each of the respective dielectric layers 11A, 11B. The graphite layers 11A, 11B substantially overlay the respective insulating layer 11A, 11B, and are oversized relative thereto.

A first conducting shield layer 9A is in contact with the graphite layer 10A, and a second conducting shield layer 9B is in contact with the optional graphite layer 10B. The first and second conducting shield layers 9A, 9B substantially conform to the shape of their respective graphite layers 11A, 11B. The graphite layers 10A, 10B may reduce triboelectric charging of the respective shield layers 9A, 9B.

In some embodiments the graphite layers 10A, 10B may be omitted.

A further insulating dielectric layer 8 is in contact with the first conducting shield layer 9A, and an insulating overlaminate 6A is in contact with this layer 8. An insulating base layer 6B is also in contact with the second conducting shield layer 9B. The overlaminate 6A and base layer 6B are configured to substantially encapsulate the other layers of the substrate, except, for example in an area about each of the plurality of sensors, if such sensors require a skin interface. In the area about the sensors that require a skin interface, the signal layer 12 may be exposed so that such sensors, for example, electrodes 1-5 can make contact with an underlying surface of the maternal patient's skin. The insulating overlaminate 6A and base layer 6B may comprise a plastics material, such as polyester. The insulating dielectric layers 8, 11A, 11B may comprise a plastics material, such as polyester or polyimide.

The base layer 6B exemplarily defines the external shape of the flexible substrate 100, and includes patch regions 21-26 exemplarily corresponding with each sensor. These sensors may include electrodes 1-5, the optical sensor 18 and any other auxiliary sensors. While the electrodes 1-5, the optical sensor 18 and any other auxiliary sensors 18 are depicted as substantially rectangular, it will be recognized that the sensors may be arranged in any shape as is suitable for the measurement obtained by such sensors. The patch regions 21-26 extend about the respective sensors associated therein. The patch regions 21-26 may be provided with an adhesive film around their perimeter, so that each patch region 21-26 can be adhered to the skin of a subject. For sensors of the plurality of sensors for which a conductive connection between the sensor and the skin of the maternal patient is needed, a conducting medium (for example ECG or acoustic gel) is preferably disposed between the sensors and the skin of the subject, thereby signally coupling the sensors to the skin of the maternal patient.

Each patch region 21-26 may include a lobe, or flap, that is substantially free from adhesive film or conducting medium and protrudes from the patch region 21-26. The lobe can be used by a clinician to hold the respective patch region 21-26 for placement, movement, or detachment of the patch region 21-26 on the maternal patient's body. Clinician gripping of the lobe helps to prevent fouling or contamination of any adhesive or conducting medium of the patch regions 21-26 or cross-contamination to the clinician from handling a patch region 21-26 that has been used.

For any polymer layer described above, a PET material may be used and has been found to provide useful properties, i.e. resilience, for avoiding breakage of the signal layer 12 during flexing of the patch in use. The material thickness of the polymer/PET layer(s) may be matched to the properties of the signal conducting layer 12 to prevent deformation of the tracks in a manner that is likely to lead to a break in the signal layer 12.

The substrate 100 comprises a reference feature 17, for lining up with an umbilicus or other suitably recognizable feature of the subject. In this case, the reference feature 17 is defined by an aperture in the flexible substrate 100. In other embodiments the reference feature 17 may be a vertex, pointer or transparent region forming in the flexible substrate 100. The reference feature 17 may be associated with an adjacent adhesive region, by which the reference feature 17 can be secured to the subject, for example adjacent to the umbilicus. As depicted in FIG. 2, the auxiliary sensor 18 may be located at a region about the reference feature 17. In embodiments when the reference feature 17 is centrally located to the patch regions 21-26, the region about the reference feature 17 may provide also provide a central and desirable location from which to measure the mechanical movement of the maternal patient and/or the fetal patient. In still further embodiments wherein an optical sensor and other auxiliary sensors 18 are used, an auxiliary sensor 18 located in the region of the reference feature 17 can be used as a reference sensor for example for noise cancellation or as an active electrode for injecting a mechanical, e.g. acoustic signal into the maternal and fetal patients.

The structure lends itself to a straightforward method of application. For example, the reference feature 17 may be secured at a reference point on the patient using the associated adhesive region. The electrodes 1-5 and respectively on regions 21-25 and an optical sensor or other auxiliary sensor 18 on region 26 can subsequently be moved away from the abdomen to prepare the skin. For example each patch regions 21-26 can then be placed in turn around the abdomen with, if necessary, suitable abrasive skin preparation. It will be recognized that while electrodes 1-5 may require a suitable electrode-skin interface, an auxiliary sensor may require such an interface, for example with a photoemitter/photosensor, an $SpO_2$ sensor, an ultrasound Doppler, a capacitive micromachined ultrasonic transducer, or a piezoelectric sensor. Other examples of auxiliary sensors, for example accelerometers, microphones, or strain gauges do not require the same electrical and/or acoustical interface with the maternal skin. Once any skin preparation, if needed, and the subsequent placement of an electrode 1-5 or auxiliary sensor has been completed the impedance of the connection between the electrode 1-5 and the patient may be measured by an electronic readout device 200 (shown in FIGS. 3 and 4). If the impedance is above a desired value, further preparation of the skin may be carried out to reduce the impedance to below the desired value. The desired value may, for example, be 5 kOhms. When the impedance is below the desired value, the skin region for the next electrode may be prepared by abrading the skin and the electrode subsequently applied electrode, and the impedance tested. This method may be repeated until all of the electrodes are successfully applied.

As depicted in FIG. 2, the auxiliary sensor 18, and more specifically, the optical sensor 18 may be located in a variety of positions relative to the rest of the patch 150. In an example, the detection of PPG and/or $SpO_2$ in photosignals requires alignment of the optical sensors with the placenta which provides the most blood pooling from the fetus blood in the uterus. The placenta may be in a similar alignment with the positioning of the biopotential sensors of the patch 150 or can be variable in its position during a pregnancy. The placenta may be either in the upper, middle, or lower portions of the uterus and may extend vertically or horizontally. Therefore, in examples, while the auxiliary sensors 18 embodying optical sensors may be integrated into the regions 21-25 adjacent to respective electrodes 1-5, in still further examples, a separate region 26 is provided to include the optical sensor 18, which for example, includes at least one photoemitter 34 and at least one or at least two photodetectors 36. The separate region 26, while it may be electrically or otherwise communicatively connected to the connection hub 16. The separate region 26 may be positioned relative to the location and orientation of the placenta for each patient and the separate region 26 provides this flexibility to tune the positioning of the region 26 to each patient. Further, the separate region 26 may be physically separate from the rest of the patch 150 and communicatively connected to provide the detected photosignals as described in further detail herein.

Figure 3:
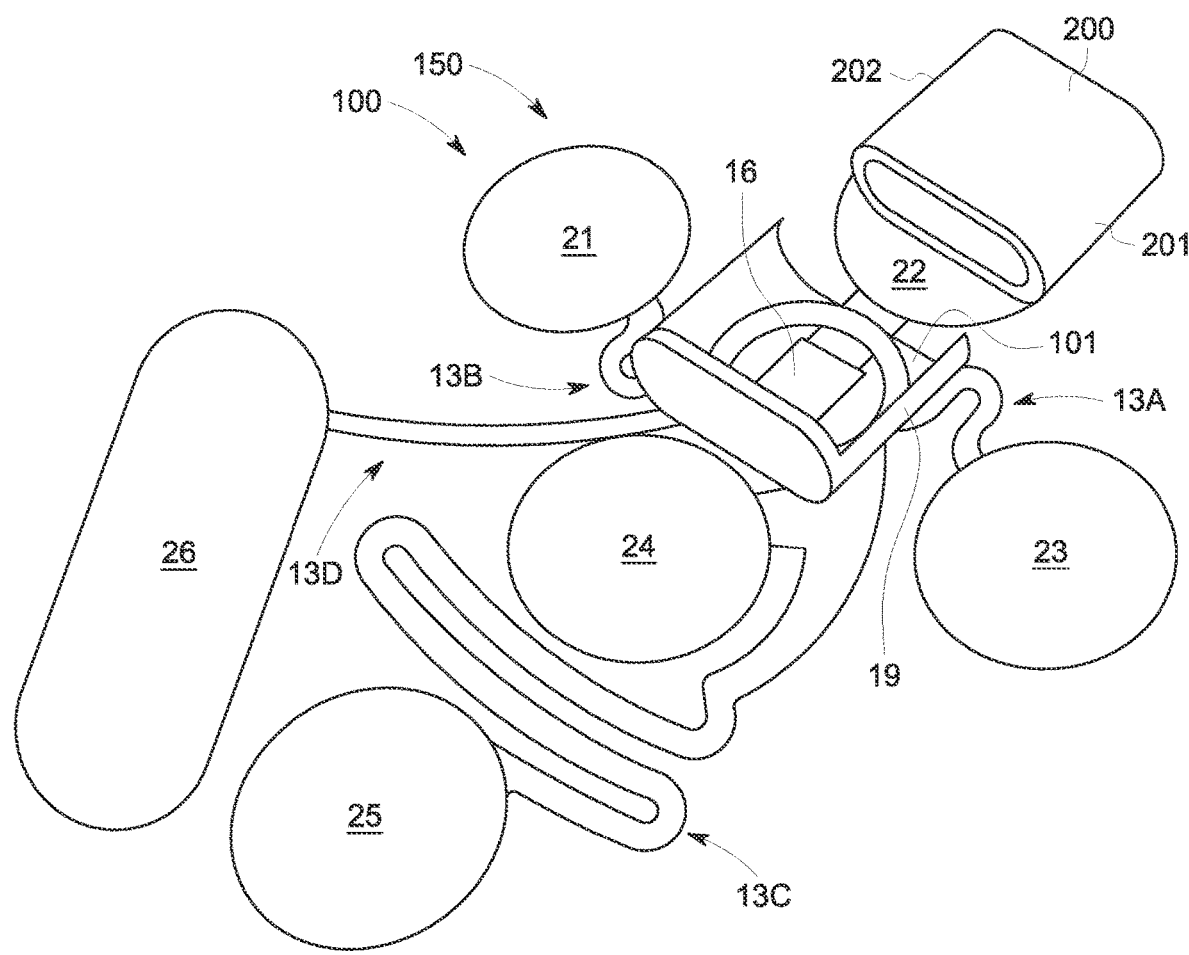
FIG. 3 is a perspective view of an exemplary embodiment of a patch and readout device.

FIG. 3 shows a top view of an exemplary embodiment of a patch 150 as depicted in FIG. 2. In this embodiment, the mechanical module unit 19 is affixed to the substrate 100 adjacent to the electrical module unit 16, as previously shown in FIG. 2. The patch 150 is shown with a separate electronic readout device 200 for detecting signals from the electrodes 1-5 and at least one auxiliary sensor 18 of the patch 150. In embodiments as described in further detail herein with respect to FIG. 4, the readout device 200 may include a processor or other processing electronics to analyze the detected signals and to produce physiological data of the fetal and maternal patients. In still further embodiments, the readout device 200 may rather serve a communicative function, providing wireless communication of the detected signals from the sensors of the patch 150 to a computer processor located remote from the patch 150. The remotely located computer processor may perform the same functions as described herein to analyze the detected signals to produce physiological data of the fetal patient and the maternal patient. In embodiments, the remotely located computer processor may be located in a same room as the maternal patient, while in other embodiments the remotely located computer processor may be a cloud or networked computer processing system wherein the detected signals are transmitted to a location further away for processing. In such embodiments, any calculated physiological data may be returned back locally for presentation to caregivers and/or the maternal patient.

The mechanical module 19 includes a cradle for receiving the readout device housing 201 of the readout device 200. The housing 201 is removably received and held within the cradle, which allows movement of the housing 201 only in the direction of insertion/removal relative to the cradle. The cradle comprises a stop, and the readout device 200 is fully engaged with the mechanical module unit 19 when the housing 201 is in contact with the stop. The mechanical module 19 further comprises a latch or catch to retain the readout device housing 201 in contact with the stop. In this embodiment the latch or catch comprises a magnetic catch. A permanent magnet is provided on either (or both) of the mechanical module 19 and housing 201, which attracts a corresponding magnet (or ferromagnetic element) on the other of the mechanical module 19 or housing 201. In alternative embodiments, a hook and loop arrangement (e.g. Velcro) may be used to secure the readout device 200 to the patch 150. In an embodiment, the magnetic catch can be used to avoid incorrect positioning of the mechanical module.

In embodiments, the readout device 200 may also include one or more auxiliary sensors as described either above or in further detail herein. Auxiliary sensors may be located in the readout device 200, particularly those auxiliary sensors which may suitably operate without an acoustic or electric connection to the maternal patient's skin. Such sensors may exemplarily include an accelerometer. In other embodiments, the readout device 200 may include a microphone, a Doppler ultrasound sensor, or a capacitive micromachined ultrasonic transducer either to collect sounds from the maternal patient or to collect ambient sounds for noise cancellation from signals obtained from a microphone arranged in the patch 150 to collect sounds of the maternal and fetal patients.

When the readout device housing 201 is fully engaged with the mechanical module 19, an electrical module 204 (shown in FIG. 5) of the readout device 200 is in electrical engagement with the electrical module 16 of the patch 150. The electrical module 204 of the readout device 200 may conveniently comprise a plurality of contacts mounted on resiliently deformable members (e.g. spring loaded contact pins).

The readout device 200 is preferably configured to calculate an output at least one of a: fHR, fECG, mHR, mECG, or UA. As described in further detail herein, the readout device may further be configured to calculate an output of at least one of fPPG, mPPG, $fSpO_2$, and $mSpO_2$. Preferably the readout device is configured to output any combination or subset of the above. The readout device is preferably configured to transmit the output, so that it can be monitored. As described in further detail herein, the readout device can calculate the above parameters from the detected biopotentials. Additionally, the readout device can calculate fHR, mHR, or UA from the signals of the at least one auxiliary sensor. As further described herein, the signals from the auxiliary sensor can further be used to calculate $fSpO_2$ and $mSpO_2$. In still further exemplary embodiments, fHR, mHR, and UA are calculated by using a combination of biopotential and auxiliary sensor signals. These calculations may weight the contribution of the biopotential signals and the auxiliary signals to the calculations of fHR, mHR, and UA while in other embodiments, the signal strengths or quality may be determined and the calculations of fHR, mHR, and UA based upon the different signals selected based upon the input signal quality. In still further embodiments the calculations may be used in combination, for example, the biopotential determination of UA may be used to help identify UA occurrence in the mechanical movement auxiliary signal while contraction strength is calculated from the mechanical movement auxiliary signal.

As previously noted, the biopotential analysis of fHR, mHR, and UA are known to be accurate, but processing systems to calculate each of these parameters from the same signals may use a delay in the output to ensure that a high-quality calculation is made. However, during some medical procedures, for example an epidural catheterization, real-time, or near real-time indications of UA and/or contraction strength, and possibly as well as fHR and mHR may be desired. In an exemplary embodiment, the combination of the signals from the biopotential sensors and the auxiliary sensors can be used to operate in an "epidural mode", producing a real-time or near real-time output of physiological parameters. In one embodiment, the signals from the biopotential sensors and the auxiliary sensors are used to increase the input information and increasing the reliability of the output produced using real-time or near-real time signal processing techniques. In another embodiment, the biopotentials are used to produce the calculations of fHR and mHR, while the auxiliary sensor signal is used to produce the calculations of the UA and contraction strength. By segmenting the determinations made from each signal, signal processing can be more specifically focused, resulting in faster calculations of each of the physiological parameter values.

In an embodiment, with detection of fHR and mHR from two different physiological properties (e.g. biopotential and mechanical motion), a comparison between these determinations can be made to further evaluate fetal and/or maternal health. By comparing the onset and occurrence of heartbeats as detected based upon electrical activity and mechanical motion, discontinuity between these two physiological observations, for example electrical impulses that produce an expected mechanical result can be observed. Detection of this anomaly can provide an early warning of serious medical conditions. In another embodiment, an estimate of maternal blood pressure can be calculated from a comparison of the maternal pulse from the mECG and maternal pulse from the pulse oximetry sensor.

One example of the multi-electrode patch includes an optical sensor in the form of an $SpO_2$ sensor as the auxiliary sensor or as at least one of a plurality of auxiliary sensors. $SpO_2$ is commonly performed by transmission oximetry. However, for incorporation as an auxiliary sensor 18 into the multi-electrode patch 100, the $SpO_2$ sensor uses reflection oximetry in which the optical emitter and the receiver optical sensor are arranged on the same side of the body. Reflection oximetry measures the light reflected back to the emitter through the skin on the same side of the patient's body as compared to transmission oximetry that measures the light from the emitter that transmits through a portion of the patient's body.

The electrical detection of fECG is typically more accurate than the optical detections of fHR, mHR, $fSpO_2$, and $mSpO_2$ from reflection PPG or reflection oximetry of the maternal and fetal patients. The fECG and mECG signals tend to be more fiducial due to the sharp R-wave for detection. However, $fSpO_2$ and $mSpO_2$ are valuable parameters for monitoring the heath of the maternal and fetal patients and fHR and mHR determinations may be available through reflection oximetry during time periods of patient monitoring when one or more biopotentials required to calculate mECG or fECG are not available. In a still further example, the PPG and or pulse oximetry of the optical signals can be used to enhance the processing of fECG and mECG in the presence of electrical or motive noise. Windowed portions of processed optical signals relative to the determined maternal or fetal pulse can be used in a similar manner to that as described herein to improve fECG and or mECG processing. Therefore, incorporation of reflection oximetry as an auxiliary sensor in the multi-electrode patch and systems and methods thereof as described herein can be complimentary to the detection of mECG and fECG.

In examples, as will be detailed herein, the processor 306 either uses the ECG directly for timing purposes in photosensor pulse detection, or uses synchronized learning between the signals from the electrical property sensors 302 and the signals from the optical sensors 304, to create a patient-specific model for use in future detection of pulses/heart rate based solely upon the signals of the optical sensors 304 (or other auxiliary sensor signals). During times when ECG can be detected (e.g. during periods of low skeletal electrical noise, low motion artifact, and/or quality electrode connections), the maternal and/or fetal ECG R-waves or QRS complexes can be determined from the ECG signals. This determination provides a precise timing of the respective HR, and the period between heart beats. With the simultaneous collection of photoplethysmograph (PPG) signals with a photoemitter/photodetector mechanical property sensors, the corresponding timing of the fetal heart beats from the R-wave or the QRS complex of the ECG can be used to improve pulse detection and later blood oxygenation analysis in the photosignals.

In an example, using the timing provided by the ECG, the photosignals are windowed into segments relative to the ECG. In an example, a window of the photosignal is taken centered on the R-wave or QRS complex of a corresponding synchronized ECG. The window may have any temporal width up to the intra-beat period of the patient at that time. It will be recognized that in further examples, the temporal width of the window may be of a shorter or longer time duration. The temporal width of the window may further be skewed relative to the R-wave or QRS complex of the ECG extending within the photosignal either further before or further after the reference point of the R-wave or QRS complex.

Figure 6:
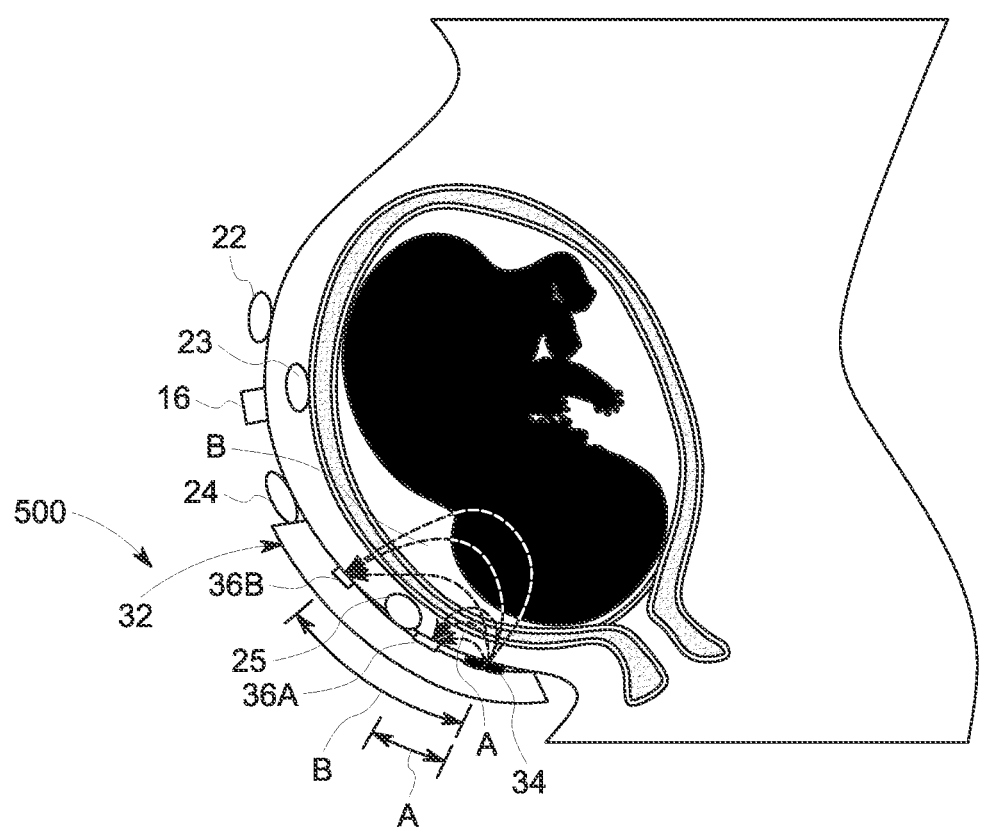
FIG. 6 is a diagrammatic view of a patch on a patient.

FIG. 6 is a schematic example of a reflective $SpO_2$ sensor 32 affixed to the abdomen of a pregnant patient. The emitter 34 (or emitters) projects light energy into the abdomen of the pregnant patient. In examples the emitter 34 projects light energy within specific wavelengths. In one example, the light energy is visible light. In another example, the light energy is red and infra-red wavelengths of light. In a still further example, red, infra-red, and green wavelengths of light are used. Other wavelengths or combinations of wavelengths will be recognized by a person of ordinary skill in the art based upon the present disclosure. It will be recognized that various combinations of wavelengths or wavelength bands could be used, such combinations could include using light at one, three, five, seven or other numbers of wavelengths or wavelength bands. Light reflected back to the same skin surface as the emitter returns at different distances A, B from the emitter 34 relative to the depth of the anatomical structure from which the light energy reflects. Photodetectors 36A and 36B are spaced apart from the emitter 34 at respective distances A and B. Distance A corresponds to light reflected from the uterine wall of the patient, while distance B corresponds to light reflected from the fetus within the uterus. In this manner, the signal obtained at photodetector 36B contains both maternal and fetal signals while the shallower reflected signal returned at photodetector 36A contains only signals from the maternal patient.

Figure 7:
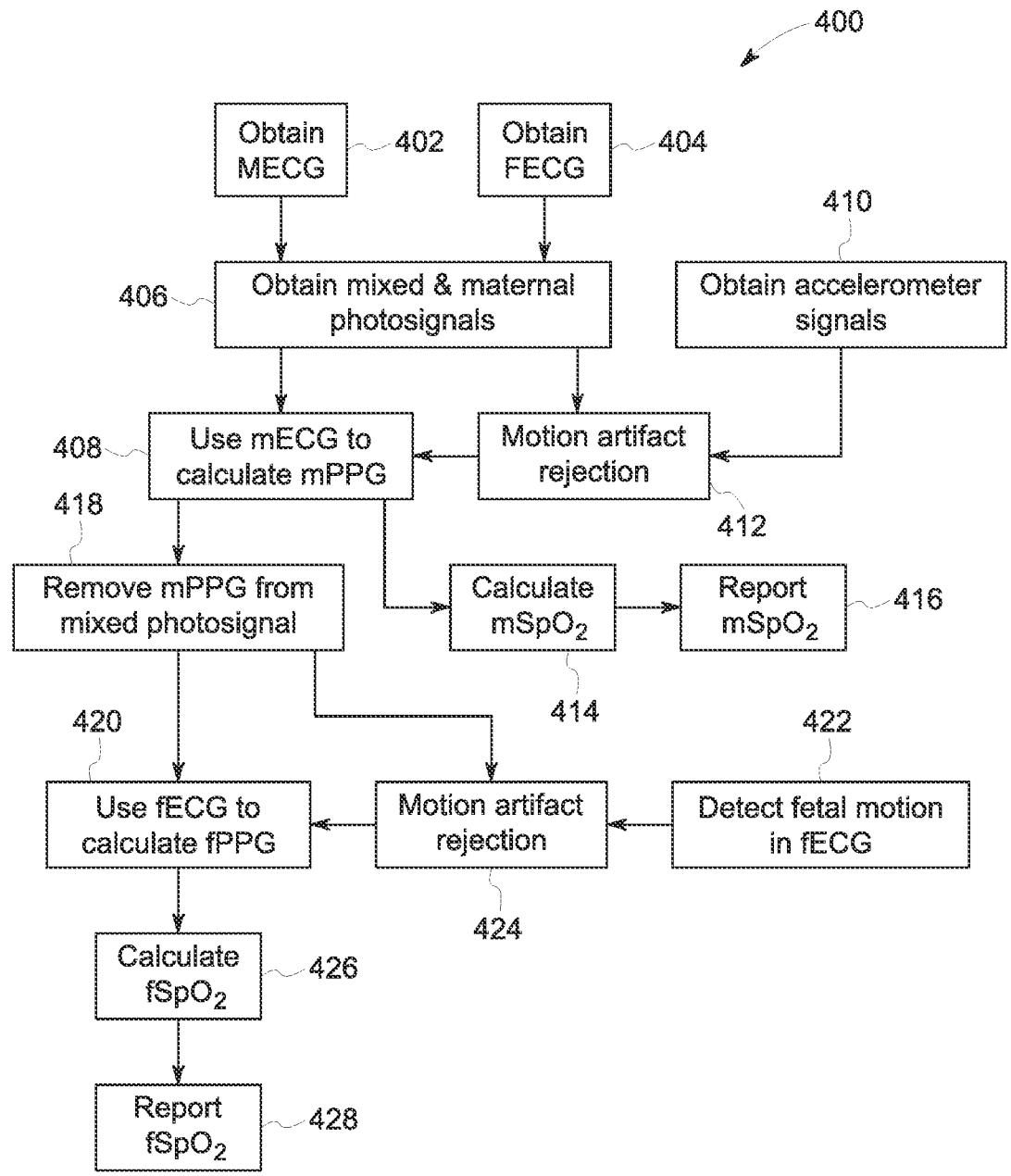
FIG. 7 is a flow chart of a method of measuring maternal and fetal $SpO_2$.

FIG. 7 is a flow chart of an example of a method 400 of determining maternal and fetal pulse rate and maternal and fetal $SpO_2$. The method 400 as well as variations thereof which will be recognized based upon the present disclosure may be carried out using the multi-electrode patch as described above. It will be recognized that pulse rate and heart rate can be treated as corresponding measurements respectively from biopotentials and photosignals. The method 400 starts at 402 where mECG is obtained and 404 where fECG is obtained. These measurements of mECG and fECG may be obtained in the manners as described above. Additionally, mixed and maternal photosignals are obtained at 406 through use of the SpO2 sensor as described above, which may be incorporated into the multi-electrode patch as described with respect to FIGS. 1-3 and 6. As noted, depending upon the distance between the photoemitter 34 and the respective photodetectors 36A, 36B, photosignal B is the mixed photosignal that contains mixed physiological data of both the maternal and fetal patients while photosignal A is the maternal photosignal and contains physiological data of only the maternal patient.

At 408, the mECG is synchronized with one or both of the mixed and the maternal photosignals. Once synchronized, the detectability of the R wave or QRS complex of the mECG is used to select a segment or window of the photosignal within which to detect the maternal pulse waves. The maternal pulse waves detected within the photosignal provide the maternal photoplethysmogram (PPG) from the photosignal. The maternal pulse rate, which corresponds to the mHR can be calculated directly from the mPPG. This provides a determination of mHR that is based upon a separate physiological property (blood flow) from the biopotential determination of mHR from the mECG.

In optional examples, the multi-electrode patch further includes an accelerometer as previously described. At 410, accelerometer signals are obtained. When the accelerometer is positioned external to and separated from the skin of the maternal patient, the obtained accelerometer signals are reflective of maternal motion. This information can be used at 412 to identify time periods of the synchronized mECG and m PPG that are likely to have motion artifacts. These portions of the PPG that are likely to have motion artifacts can either be rejected altogether (e.g. in creating an mPPG detection model, or calculating $SpO_2$ as described herein) or may receive additional signal processing to attempt to mitigate the motion artifact for continued use of the information.

Whether or not motion artifacts are identified and rejected or mitigated as described, the mPPG is used to calculate $mSpO_2$ at 414. Once the $mSpO_2$ is calculated, at 416 it may be visually reported, for example on the display 310 or stored in the patient EMR 312 (See FIG. 1). Maternal pulse rate (mHR) calculated from the mPPG can also be similarly reported. In one example, at 408, the mPPG is calculated separately from both the mixed photosignal and from the maternal photosignal. In such an example, the $mSpO_2$ is calculated from the mPPG from the maternal photosignal. Since the maternal photosignal does not contain signals from the fetal pulses, the maternal photosignal can provide a more fiducial representation of maternal pulses than the mixed photosignal. However, the mPPG is also calculated from the mixed photosignal as described herein for use in further signal processing and evaluation of the fetal patient physiological condition.

At 418, the mPPG (as determined based upon the maternal contribution to the mixed photosignal) is removed from the mixed photosignal to leave the mixed photosignal with the signal portions with the fetal pulse contributions. Similar to that as described above, with the fECG synchronized with the mixed photosignal, the R waves and/or QRS complexes of the fECG signal are used to select segments or windows of the mixed photosignal within which to detect the fetal pulse waves at 420. The fetal pulse waves detected within the mixed photosignal are used to calculate the fetal photoplethysmogram (fPPG) from the mixed photosignal. The fetal pulse rate, which corresponds to the fHR can be calculated directly from the fPPG. This provides a determination of fHR that is based upon a separate physiological property (blood flow) from the biopotential determination of fHR from the fECG.

In optional examples, at 422, the fECG signal is used to identify time periods of the synchronized fECG and fPPG that are likely to have fetal motion artifacts. These portions of the fPPG that are likely to have fetal motion artifacts can either be rejected altogether (e.g. in creating an fPPG detection model, or calculating $fSpO_2$ as described herein) or may receive additional signal processing to attempt to mitigate the motion artifact for continued use of the information at 424. In a still further example, the maternal motion artifact detection as described above at 410 and 41 may be used to identify, remove, and/or mitigate maternal motion artifacts from the fPPG.

Whether or not motion artifacts are identified and rejected or mitigated as described, the fPPG is used to calculate $fSpO_2$ at 426. Once the $fSpO_2$ is calculated, at 428, the $fSpO_2$ may be visually reported, for example on the display 310 or stored in the patient EMR 312 (See FIG. 1). Fetal pulse rate (fHR) calculated from the fPPG can also be similarly reported.

The method 400 above has primarily focused on the direct use of synchronization between the mECG/fECG signals and the corresponding mixed photosignal or maternal photosignal. However, in other examples, the synchronized ECG and photosignals are used to create models or templates of the maternal PPG pulses and the fetal PPG pulses for use in detection of fHR, mHR, $fSpO_2$, and $mSpO_2$, even in the absence of a synchronized ECG signal.

The segments of the maternal and fetal PPG, are identified and obtained as described above during times when the corresponding synchronized fECG/mECG signal is also available. Any segments determined to have motion artifacts are rejected and the remaining segments are used to create a model of the respective maternal or fetal pulses in the time or frequency domain. This model of the pulses is exemplarily specific to the fetal and maternal patients being monitored and can be developed over time during monitoring the maternal and fetal patients. When use to determine mPPG and fPPG, as well as the resulting fHR, mHR, $fSpO_2$, and $mSpO_2$ therefrom, such model-based determination may be more accurate in determining an intra-beat heart rate compared to using other signal processing techniques, for example autocorrelation, which results in an average value for fHR.

In examples, the fetal and maternal pulse models are created (and updated) while quality data is obtained from the fECG, mECG, fPPG, and mPPG signals. Then when fECG is lost (e.g. during a period of high skeletal noise) fHR can be determined directly from the fPPG by applying the fetal pulse model to the mixed photosignals.

In a still further example, the synchronized ECG and photosignals are used to enhance the processing and determination of mECG/fECG from the biopotential signals, particularly in the presence of noise in the biopotential signals. Windowed portions of processed photosignals relative to the determined maternal or fetal pulse in the PPG or $SpO_2$ can be used in a similar manner to that as described above to improve fECG and or mECG processing. Windows of the biopotential signal corresponding to the maternal and or fetal pulses detected in the photosignals can be used to focus the analysis to the windowed portion of the biopotential signals in determining the mECG/fECG.

As noted above, a variety of types of sensors may operate to serve as the other auxiliary sensors in the present disclosure. However, some types of sensors are better suited for detection of various physiological parameters than others. While a microphone can be used to detect fetal motion, mHR, or fHR, the collected sound waves are unsuited to detect uterine activity or contraction strength. Strain gauges are well suited to detect UA and contraction strength, but are not able to be used to detect mHR, fHR, or fetal motion. Ultrasonic sensors and piezoelectric sensors can be used to detect all of the above noted fetal motion, mHR, fHR, UA, and contraction strength. However, ultrasonic sensors require an external power source to produce the emitted ultrasound signal and require a specialized acoustical interface with the skin of the maternal patient. Therefore, embodiments using ultrasound may impede the disposable and ease-of-use advantages of current embodiments of the monitoring patch device.

Embodiments of auxiliary sensors including microphones, strain gauges, and piezoelectric sensors can all be printed using conductive inks, for example silver-containing inks, in the manners as noted above with respect to the construction of other components of the patch. Therefore, microphones, strain gauges, and piezoelectric sensors may be incorporated into the patch without significant change to the manufacturing techniques currently used to construct the patch. In one embodiment, at least one, if not a plurality of piezoelectric sensors are incorporated into the patch as described above and signals representative of fetal motion, mHR, fHR, UA, and contraction strength collected therefrom. In another exemplary embodiment at least one microphone and at least one strain gauge are incorporated into the patch as described above and signals representative of fetal motion, mHR, fHR, are collected from the at least one microphone, while signals representative of UA and contraction strength are collected from the at least one strain gauge.

In further embodiments, additional functionality may be added to the patch device as described herein with the incorporation of additional types of auxiliary sensors either into the patch substrate as described with respect to FIG. 2 or incorporated into the readout device 200 as described with respect to FIG. 3. These additional auxiliary sensors may include, but are not limited to, a temperature sensor or an SpO$_2$ sensor. A temperature sensor may be a thermistor or a thermocouple and when placed in contact with the maternal patient's skin can be used to provide an ongoing presentation of maternal temperature, for example to determine if the maternal patient is becoming too hot or too cold. The SpO$_2$ sensor uses a small light emitting diode (LED) to project red and/or infra-red light into the patient to measure the amount of light in this spectrum that is absorbed, producing an indication of the Oxygen saturation of the patient's blood.

In still further embodiments, the controller (FIG. 1), the readout device (FIG. 3), or a communicatively connected computer may perform additional computational signal processing on the collected signals from the aforementioned sensors incorporated into the patch. This additional signal processing may be of the biopotential signals or may be of the sensors from the auxiliary sensors. Additional signal processing of the biopotential signals may be used to detect maternal or fetal EEG or to produce a more robust fECG or mECG analysis, including morphological analysis. Both biopotential signals and signals from the auxiliary sensor may be used to detect respiration rate, either as a motion artifact to biopotential signals or as respiratory sounds from a microphone, or respiratory abdominal movement in a piezoelectric sensor, a strain gauge, or an accelerometer. Additionally, signals from the auxiliary sensor suitable to detect fetal motion can also be further processed to detect the specific fetal motion of a kick to produce a kick count, which has been linked to an evaluation of fetal health.

Preferably, the readout device 200 comprises a wireless transmitter (e.g. according to the Bluetooth standard), operable to transmit the output of the readout device 200.

In some embodiments, the readout device 200 does not calculate any of the physiological data as noted above, but rather transmits raw or partially processed voltage and/or current data from the sensors, for processing by a further device into a suitable output (such as one, two, three, four or more of a fetal heart rate, fetal ECG, maternal heart rate, maternal ECG, or uterine activity).

Figure 4:
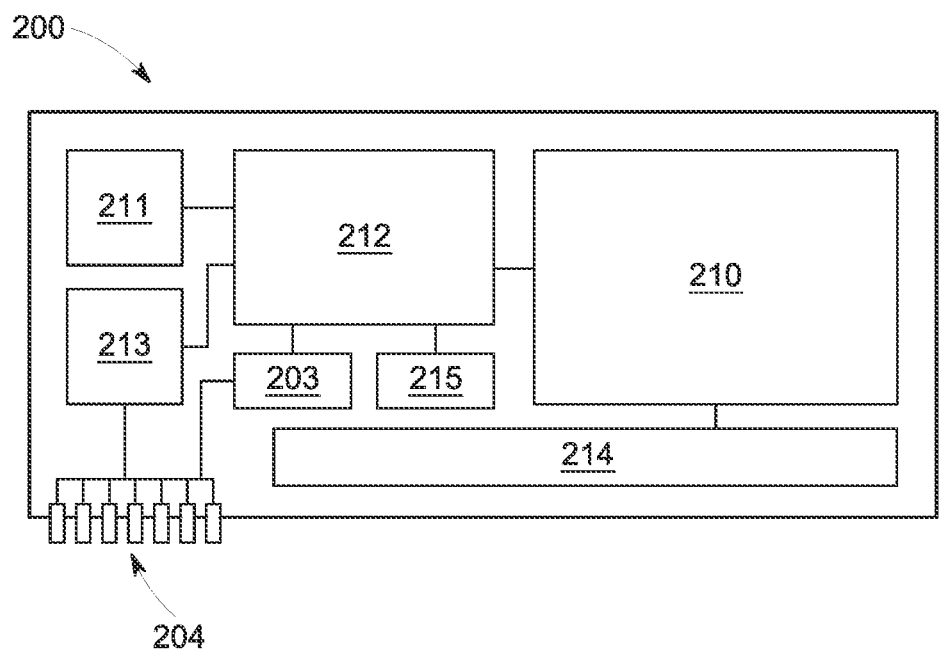
FIG. 4 is a block diagram of an exemplary embodiment of a readout device.

Referring to FIG. 4, a block diagram of a readout device 200 according to an embodiment is shown. The readout device 200 of FIG. 4 exemplarily presents a more detailed embodiment of the components of the controller as shown and described above with respect to FIG. 1. The readout device 200 comprises an electrical module unit 204, analog circuit 213, digital processor 212, wireless transmitter 211, security device 203, battery 210, and an inductive coil 214.

The analog circuit 213 includes an analog to digital converter, and receives the electrical signals from the electrodes and any electrical measurement signals from the mechanical movement sensors, and outputs a digitized version thereof, for processing by the digital signal processor. In some embodiments the analog circuit 213 may include an amplifier and/or filter.

The processor 212 receives a digitized signal from the analog circuit 213, and preferably processes it to determine an output, as described already. The processor 212 subsequently outputs a signal to the wireless transmitter 211 for onward transmission, for example to a receiving and display station 300 according to an embodiment of the invention.

In order to maximize the battery life of the removable electronic device it may be configured such that the power of the wireless transmitter is controlled based upon the signal strength index and/or bit error rate. This may greatly lengthen the monitoring period that can be carried under one single battery charge.

In some embodiments, one or more component of the device 200 may be combined, for example in a multi-chip module or system on chip. For example, the processor 212 may comprise any combination of the analog circuit 213, the security device 203 and the wireless transmitter 211.

The electronic components of the readout device 200 are powered by an electrical power source, which is a battery 210 in this embodiment. In other embodiments the electrical power source may comprise a capacitor. The inductive coil 214 is operative to charge the battery 210 or to power the readout device directly, optionally under the control of the processor 210.

The readout device 200 may be configured to detect electrophysiological signals between a pair of sensing electrodes, rather than simply between a sensing electrode and the common electrode. For example, the readout device 200 may be configured to detect electrophysiological signals between sensing electrodes 1 and 3 (i.e. horizontally across the abdomen in use). This allows a further channel of UA and fetal ECG to be provided. The advantages for UA are that the separation is relatively fixed between electrodes 1 and 3 and hence this offers the potential of indicating contraction strength. Furthermore, such a horizontal fECG channel (measured between sensing electrodes 1 and 3)

allows breech and transverse presentations to be more carefully monitored. In addition, by providing this channel a further Maternal ECG channel can be generated that can be used for mECG removal, further reducing confusion between the mECG and fECG. The use of another mECG channel (for example, measured between sensing electrodes 1 and 3) can further reduce this confusion by providing an improved template for accurate mECG removal.

The readout device 200 may comprise sensors 215, which may comprise an inertial sensor such as accelerometer and/or gyroscope. Preferably, the sensors 215 comprise a one, two or three axis accelerometer, and/or a one, two or three axis gyroscope. The sensors 215 may be MEMS (micro-electromechanical systems) devices. The readout device 200 may comprise an inertial measurement unit. The accelerometers and gyroscopes may be used to track the movement of the readout device 200, thereby allowing both fetal ECG and electrohysterogram algorithms to differentiate between maternal/fetal movements and genuine contractions and fetal ECG signals and allowing to identify maternal pushing during the second stage of labor. A gyroscope can provide useful additional rotational information that an accelerometer cannot provide, thereby allowing further separation of fetal movement from the acquired data. This fetal movement is a highly useful indicator that provides further fetal well-being indication. Additionally the use of the pair of devices allows separation of the maternal breathing signal which is a further indication of maternal health.

Figure 5:
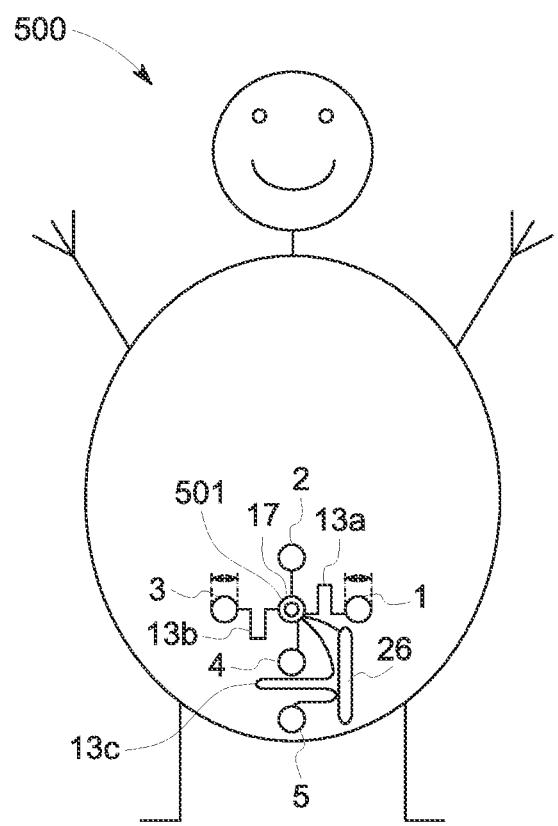
FIG. 5 is a schematic of a test subject and a patch in use on a patient.

Referring to FIG. 5, a patch 150 according to an embodiment of the invention is shown in use, applied to the abdomen of a pregnant human subject 500. The skin is preferably prepared to ensure a good contact is made between each electrode and the skin, and gel is preferably applied to electrically couple the electrodes to the skin. The reference feature 17 of the patch is aligned with the umbilicus 501 of the subject 500, and the first sensing electrode 1 and drive electrode 4 are arranged on the abdomen on the median plane of the subject. The common electrode 5 is placed facing the symphis pubis, by extending the flexible substructure 13C if necessary. The patch 150 is comfortable and low profile, and relative movement of the electrodes (e.g. as a result of breathing and locomotion) is accommodated. The patch 150 schematically represents features as previously shown and described above. The patch 150 of FIG. 5 depicts the electrodes 1-5 as well as region 26 which exemplarily includes the optical sensor. The region 26 is sized and dimensioned so as to provide the spacing required between the photoemitters and the photodectectors for the reflection oximetry as described above.

The integration of the readout circuit 200 and patch 150 allows the subject to move freely, without having to worry about leads, and minimizing any deleterious cable noise that can arise due to triboelectric effects when leads are flexed. Furthermore, the short length of the connections to the readout circuit minimize the potential for other sources of noise.

The readout device 200 preferably comprises a wireless transmitter (not shown), and is operable to wirelessly transmits the output, via the wireless transmitter, substantially in real time, to a monitoring station that is operable to display the output. The readout device 200 is compatible with a number of monitoring stations, but is preferably used with a receiving and display station 300 according to an embodiment of the invention.

Exemplary embodiments of the sensor patch and monitoring systems including the patch as described herein may be used to monitor maternal and fetal patients in a variety of settings. Embodiments may be used to monitor the progression of term and pre-term labor. However, other embodiments may be used to monitor neonatal fetal development, pre-term fetal development, and term fetal development. The disposability of the sensor patch embodiments, and ease of use enable connection of such embodiments for patient monitoring over a short period of time, for example an hour, during a routine pregnancy exam, while the design and wireless communication facilitate patient ambulation for monitoring of maternal and fetal patients under hospital observation. Still further embodiments, may be used for home monitoring and evaluation, for example during pre-labor, or early labor stages prior to the maternal patient arriving at a hospital, or for monitoring during home delivery.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of sensing the heart rate and blood oxygen saturation of a maternal patient and a fetal patient, the method comprising:
   providing a multi-sensor patch to the abdomen of a maternal patient, the multi-sensor patch configured for simultaneous abdominal monitoring of maternal and fetal physiological data;
   wherein the multi-sensor patch comprises:

a multi-layer flexible substrate comprising a center region and a plurality of electrode regions, a conductive layer of the flexile substrate providing an electrical connection between each of the plurality of electrode regions and the center region;

a plurality of electrodes formed into the flexible substrate with an electrode of the plurality of electrodes located in each of the electrode regions, each of the electrodes configured to produce the biopotential data; and an optical sensor comprising a plurality of photoemitters and a plurality of photodetectors to produce the photosignal data and a pulse oximetry sensor that is connected to the multi-layer flexible substrate;

obtaining maternal electrocardiogram (mECG) data and fetal electrocardiogram (fECG) data with the plurality of electrodes;

obtaining photosignal data with the optical sensor, the photosignal data comprising a maternal photosignal component and a fetal photosignal component;

applying mECG to the photosignal data to calculate maternal photoplesthysmograph (mPPG) data;

applying the mPPG to the photosignal data to remove the maternal photosignal component from the photosignal data; and applying the fECG to remaining photosignal data to calculate fetal photoplesthysmograph (fPPG) data.

2. The method of claim 1, wherein applying the mECG further comprises:
synchronizing the mECG data, fECG data, and the photosignal data;
identifying R waves in the mECG data and the fECG data;
using R waves from the mECG data to select portions of the photosignal data associated with maternal pulses; and
using R waves from the fECG data to select portions of the photosignal data associated with fetal pulses.

3. The method of claim 1, further comprising:
calculating mSpO2 from the mPPG data; and
calculating fSpO2 from the fPPG data.

4. The method of claim 1, further comprising:
calculating mHR from the mPPG data; and
calculating fHR from the fPPG data.

5. The method of claim 1, wherein the multi-sensor patch further comprises an auxiliary region of the multi-layer flexible substrate and wherein the auxiliary region comprises the plurality of photoemitters and the plurality of photodetectors;
wherein the photosignal data comprises first photosignal data from a first photodetector, the first photosignal data comprising a first maternal photosignal component, and the photosignal data comprises second photosignal data from a second photodetector, the second photosignal data comprising a second maternal photosignal component and a fetal photosignal component.

6. The method of claim 1, further comprising:
obtaining acceleration data from an accelerometer connected to the multi-layer flexible substrate;
determining maternal motion artifacts from the acceleration data; and
rejecting portions of the photosignal data based upon the determined maternal motion artifacts.

7. The method of claim 1, further comprising:
determining fetal motion artifacts in the fECG data; and
rejecting portions of the photosignal data based upon the determined fetal motion artifacts.

8. A system for sensing a heart rate and blood oxygen saturation of a maternal patient and a fetal patient comprising
a multi-sensor patch configured to be applied to the abdomen of a maternal patient, the multi-sensor patch configured for simultaneous abdominal monitoring of maternal and fetal physiological data, the multi-sensor patch including:
a multi-layer flexible substrate comprising a center region and a plurality of electrode regions, a conductive layer of the flexile substrate providing an electrical connection between each of the plurality of electrode regions and the center region;
a plurality of electrodes formed into the flexible substrate with an electrode of the plurality of electrodes located in each of the electrode regions, each of the electrodes configured to produce the biopotential data; and
an optical sensor comprising a plurality of photoemitters and a plurality of photodetectors to produce the photosignal data, and
one or more processors configured to:
obtain maternal electrocardiogram (mECG) data and fetal electrocardiogram (fECG) data with the plurality of electrodes;
obtain photosignal data with the optical sensor, the photosignal data comprising a maternal photosignal component and a fetal photosignal component;
apply mECG to the photosignal data to calculate maternal photoplesthysmograph (mPPG) data;
apply the mPPG to the photosignal data to remove the maternal photosignal component from the photosignal data;
apply the fECG to remaining photosignal data to calculate fetal photoplesthysmograph (fPPG) data.

9. The system of claim 8, wherein applying the mECG further comprises:
synchronizing the mECG data, fECG data, and the photosignal data;
identifying R waves in the mECG data and the fECG data;
using R waves from the mECG data to select portions of the photosignal data associated with maternal pulses; and
using R waves from the fECG data to select portions of the photosignal data associated with fetal pulses.

10. The system of claim 8, wherein the one or more processors are configured to:
calculate mSpO2 from the mPPG data; and
calculate fSpO2 from the fPPG data.

11. The system of claim 8, wherein the one or more processors are configured to:
calculate mHR from the mPPG data; and
calculate fHR from the fPPG data.

12. The system of claim 8, wherein the multi-sensor patch further comprises an auxiliary region of the multi-layer flexible substrate and wherein the auxiliary region comprises the plurality of photoemitters and the plurality of photodetectors;
wherein the photosignal data comprises first photosignal data from a first photodetector, the first photosignal data comprising a first maternal photosignal component, and the photosignal data comprises second photosignal data from a second photodetector, the second photosignal data comprising a second maternal photosignal component and a fetal photosignal component.

13. The system of claim 8, wherein the one or more processors are configured to:

obtain acceleration data from an accelerometer connected to the multi-layer flexible substrate;
determine maternal motion artifacts from the acceleration data; and
reject portions of the photosignal data based upon the determined maternal motion artifacts.

14. The system of claim 8, wherein the one or more processors are configured to:
determine fetal motion artifacts in the fECG data; and
reject portions of the photosignal data based upon the determined fetal motion artifacts.

* * * * *